(12) United States Patent
Gauvry

(10) Patent No.: US 6,402,712 B1
(45) Date of Patent: Jun. 11, 2002

(54) DUAL ACTION KNEE STRAP

(75) Inventor: George R. Gauvry, Westampton, NJ (US)

(73) Assignee: Cho-Pat, Inc., Hainesport, NJ (US)

( * ) Notice: Subject to any disclaimer, the term of this patent is extended or adjusted under 35 U.S.C. 154(b) by 0 days.

(21) Appl. No.: 09/374,688

(22) Filed: Aug. 16, 1999

(51) Int. Cl.[7] ............................. A61F 5/00; A61F 13/00
(52) U.S. Cl. .......................................... 602/26; 602/62
(58) Field of Search .............................. 602/5, 23, 26, 602/60–62, 75; 128/881, 882; 2/22, 24

(56) References Cited

U.S. PATENT DOCUMENTS

| | | | | |
|---|---|---|---|---|
| 2,270,685 A | * | 1/1942 | Miller ........................ | 602/62 |
| 3,677,265 A | | 7/1972 | Brabazon | |
| 4,250,578 A | | 2/1981 | Barlow | |
| 4,287,885 A | | 9/1981 | Applegate | |
| 4,296,744 A | | 10/1981 | Palumbo | |
| 4,334,528 A | * | 6/1982 | Gauvry ........................ | 602/26 |
| 4,370,978 A | | 2/1983 | Palumbo | |
| 4,423,720 A | | 1/1984 | Meier et al. | |
| 4,466,428 A | | 8/1984 | Mc Coy | |
| 4,724,831 A | * | 2/1988 | Huntjens ..................... | 602/26 |
| 4,765,318 A | | 8/1988 | Tranberg et al. | |
| 5,016,621 A | | 5/1991 | Bender | |
| 5,024,216 A | | 6/1991 | Shiono | |
| 5,334,135 A | | 8/1994 | Grim et al. | |
| 5,417,646 A | | 5/1995 | Gauvry | |
| 5,527,267 A | * | 6/1996 | Billotti ........................ | 602/13 |
| 5,613,943 A | | 3/1997 | Palumbo | |
| 5,733,249 A | * | 3/1998 | Katzin ........................ | 602/21 |
| 5,759,167 A | * | 6/1998 | Shields, Jr. ................. | 602/26 |

* cited by examiner

Primary Examiner—Denise Pothier
(74) Attorney, Agent, or Firm—Norman E. Lehrer

(57) ABSTRACT

A knee strap which includes a main body portion having a first side, a second side, a front, and a back; a first pair of arms extending from and attached to the first side of the main body portion; and a second pair of arms extending from and attached to the second side of the main body portion is disclosed. The first pair of arms includes a top arm and a bottom arm where each arm has a rubber tube enclosed therein. The top arm fits above the kneecap and the bottom arm fits below the kneecap. The tubes apply pressure to the tendons located above and below the kneecap once the strap is secured on a person's knee. The first pair of arms is held in place on a person's knee with hook and loop fasteners which are located on both the first pair of arms and the second pair of arms. The second pair of arms also has a top arm and a bottom arm so that the top arms are secured together and the bottom arms are secured together. Once the arms are secured together on the knee, an opening is formed which exposes the kneecap and allows the knee to move freely yet still be supported.

6 Claims, 3 Drawing Sheets

DUAL ACTION KNEE STRAP

BACKGROUND OF THE INVENTION

The present invention is directed toward a dual action knee strap and more particularly, toward a knee strap for supporting the patella and patellar tendons located above and below the kneecap while still allowing unencumbered use of the knee.

Injury to the knee and the surrounding area including the patella and patellar tendons is frequent because the knee is a high stress area. As such, many braces have been designed and developed to give support to the knee and the surrounding area during exercise. Usually such a support is used after an injury to partially immobilize the weakened knee for preventing the possibility of further injury. Knee supports have also been designed to alleviate the pain and discomfort due to conditions such as Chondromalacia patella syndrome, patellar tendonitis, and other knee disfunctions.

Knee supports range in design from very small straps to highly involved and cumbersome rigid braces. The prior art discloses many knee brace designs which provide adequate support to the knee but fail to allow the user to move the knee in the desired or necessary fashion during certain exercises. In contradistinction, the less involved braces such as simple straps allow flexibility but don't supply the necessary support. Known knee straps that do provide adequate support restrict flexibility. Also, many of the prior art knee supports do not alleviate the pain or reduce the likelihood of some of the commonly occurring conditions involving the knee.

For example, U.S. Pat. No. 4,370,978 to Palumbo discloses a knee brace with an elastic sleeve having an opening for the kneecap. The brace has two elastic straps which wrap around the kneecap. One of the. straps has a patellar ligament pad which may be made from foam rubber and is sandwiched between a sheet of thin, pliable leather or another suitable material and the inner band surface of the strap. The knee brace disclosed in this patent, however, does not provide proper support for the knee and it is large, making the brace uncomfortable to wear.

Applicant's patent, U.S. Pat. No. 5,417,646, discloses a knee support with a main body portion which covers the kneecap and securing straps which extend from each side of the main body portion. The straps are wrapped around the knee and are secured at the back of the knee. Attached to the main body portion above and below the kneecap are pressure application straps which may be used to adjust the support given to the kneecap and patellar tendons below the kneecap. The present invention is an improvement over this patent in that pressure is applied to the tendon above the kneecap as well as the tendon below the kneecap.

SUMMARY OF THE INVENTION

The present invention is designed to overcome the deficiencies of the prior art discussed above. It is an object of the present invention to provide a device which is comfortable to wear and allows full mobility of the knee while also providing the necessary support for the knee.

It is a further object of the present invention to provide a device with two arms which provide pressure to the tendons above and below the kneecap.

In accordance with the illustrative embodiments demonstrating features and advantages of the present invention, there is provided a device which includes a main body portion having a first side, a second side, a front side, and a back side; a first pair of arms extending from and attached to the first side of the main body portion; and a second pair of arms extending from and attached to the second side of the main body portion. The first pair of arms includes a top arm and bottom arm where each arm has means for applying pressure to the patellar tendons by means of a rubber buttress inserted between layers of material in the arms nearer the skin. The top arm fits above the kneecap and the bottom arm fits below the kneecap. The first pair of arms is held in place on a person's knee by securing means which are located on both the first pair of arms and the second pair of arms. The second pair of arms also has a top arm and a bottom arm so that the top arms are secured together and the bottom arms are secured together. Once the arms are secured together on the knee, an opening is formed which exposes the kneecap and allows the knee to move freely yet still be supported.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities.

DETAILED DESCRIPTION OF THE PREFERRED EMBODIMENT

Figure 3:
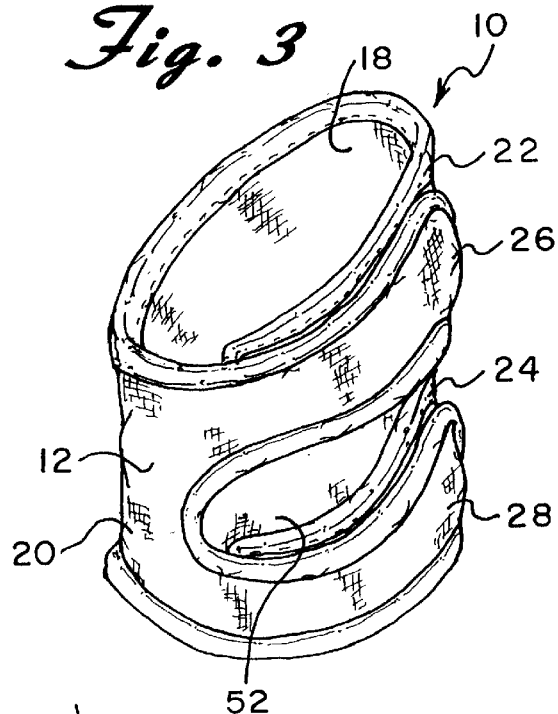
FIG. 3 is a perspective view of the dual action knee strap of the present invention.

Referring now to the drawings in detail wherein like reference numerals have been used throughout the various figures to designate like elements, there is shown in FIG. 3 a knee strap constructed in accordance with the principles of the present invention and designated generally as 10.

Figure 2:
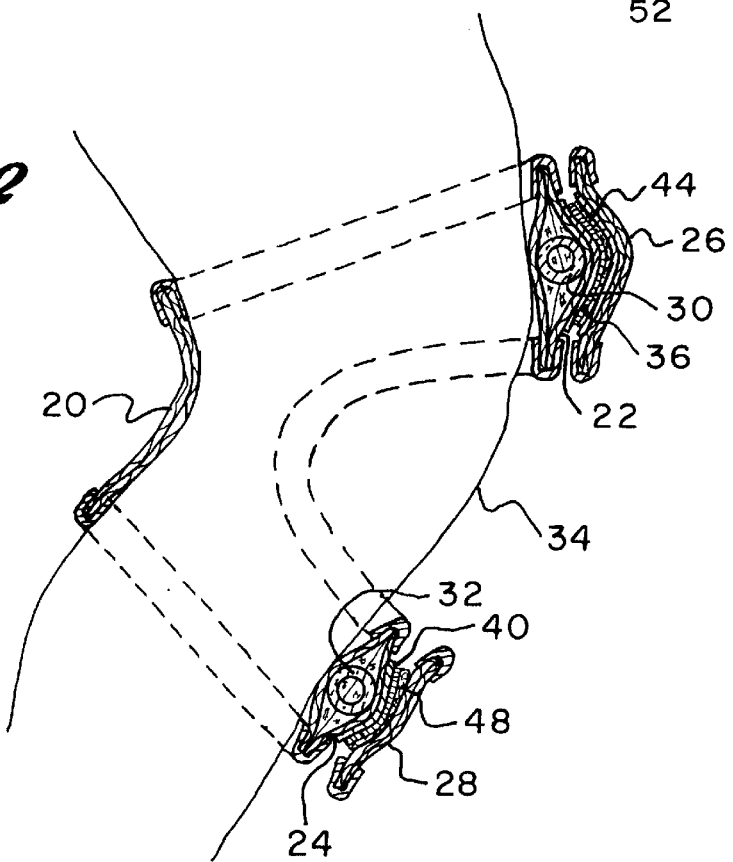
FIG. 2 is a partial cross-sectional view of the dual action knee strap of the present invention while it is being worn by a person.
Figure 7:
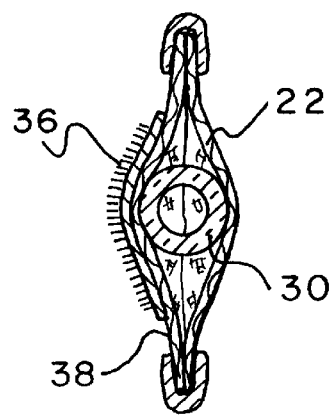
FIG. 7 is a cross-sectional view of the present invention taken along line 7—7 of FIG. 4.
Figure 8:
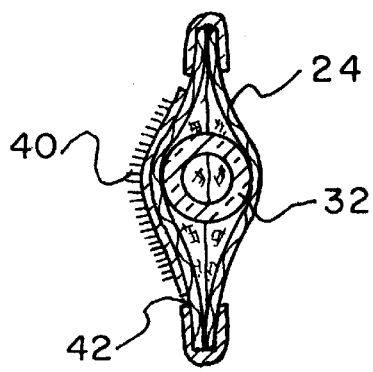
FIG. 8 is a cross-sectional view of the present invention taken along line 8—8 of FIG. 4.
Figure 9:
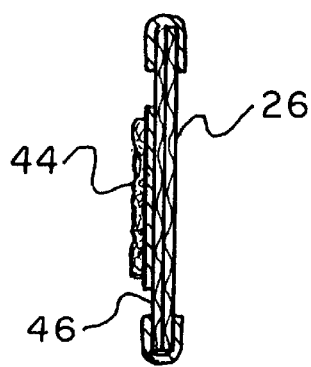
FIG. 9 is a cross-sectional view of the present invention taken along line 9—9 of FIG. 4.
Figure 10:
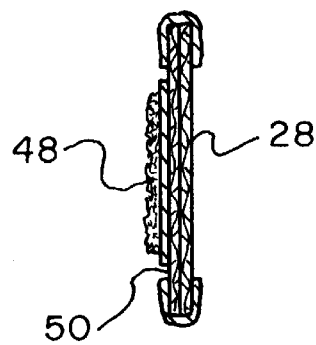
FIG. 10 is a cross-sectional view of the present invention taken along line 10—10 of FIG. 4.

The dual action knee strap includes a main body portion 12 having a first side 14, a second side 16, a front side 18, and a back side 20. The strap also has a first pair of elongated arms 22 and 24 extending from and attached to the first side 14 of the main body portion 12, and a second pair of elongated arms 26 and 28 extending from and attached to the second side 16 of the main body portion 12. The first pair of arms consists of a top arm 22 and a bottom arm 24 which are spaced apart from each other and both of which have sandwiched between two layers of material, a compressible buttress in the form of a rubber tubing preferably having an outer diameter of approximately three-eighths of an inch. Likewise, the second pair of arms has a top arm 26 and a bottom arm 28 which are spaced apart from each other. Top arm 22 and bottom arm 24 of the first pair of arms have means for applying pressure to the patellar tendons above and below a person's kneecap 34. (See FIG. 2.) These means are the rubber tubes 30 and 32 enclosed within each of the arms 22 and 24, respectively. The tubes 30 and 32 are located only in arms 22 and 24, respectively. (See FIGS. 7 and 8.) The top arm 22 fits above the kneecap 34 and the bottom arm 24 fits below the kneecap 34. The tubes 30 and 32 apply pressure to the tendons located above and below the kneecap, respectively, once the strap is secured on a person's knee, as will be described in more detail below. Although the compressible buttresses are preferably in the form of rubber tubes, it should be readily apparent that other forms could also be used such as flexible rods of resilient foam material or the like.

Figure 4:
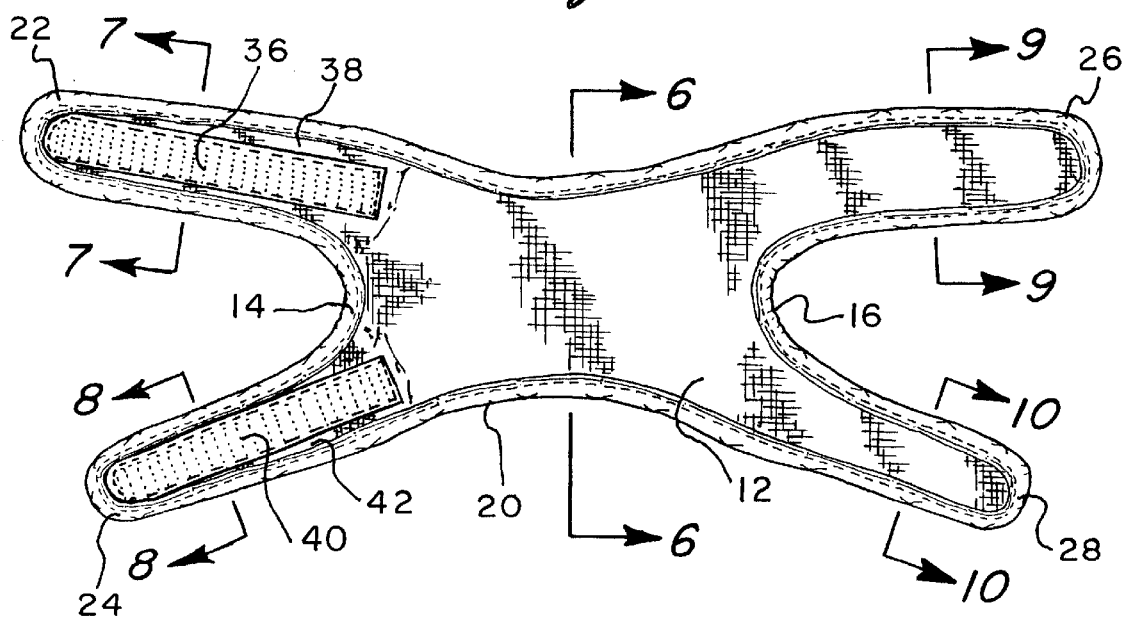
FIG. 4 is rear elevational view of the dual action knee strap of the present invention.
Figure 5:
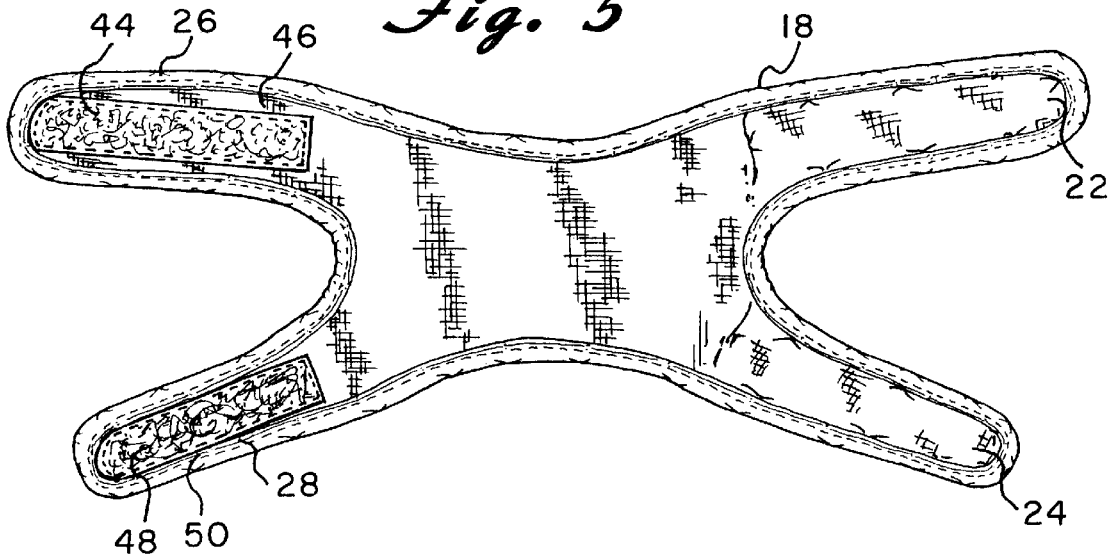
FIG. 5 is a front elevational view of the dual action knee strap of the present invention.
Figure 6:
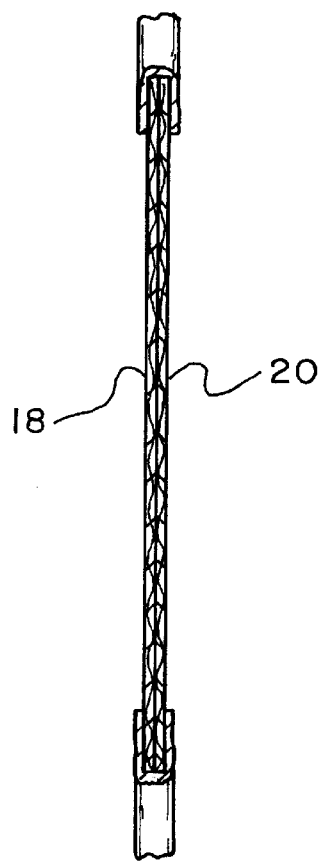
FIG. 6 is a cross-sectional view of the present invention taken along line 6—6 of FIG. 4.

The first and second pairs of arms have means for securing the top arms 22 and 26 together and the bottom arms 24 and 28 together on the front side of the knee. Such means may include hook and loop fasteners, for example, VELCRO strips. That is, a VELCRO strip 36 may be attached to the back side 38 of the top arm 22 and a VELCRO strip 40 may be attached to the back side 42 of the bottom arm 24. (See FIG. 4.) A VELCRO strip 44 may also be attached to the front side 46 of the top arm 26 and a VELCRO strip 48 may be attached to the front side 50 of the bottom arm 28. (See FIG. 5.)

Figure 1:
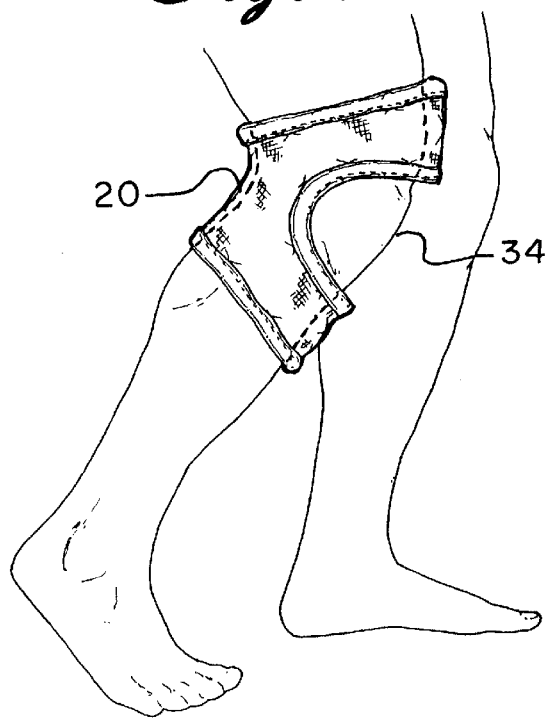
FIG. 1 is a schematic representation of the dual action knee strap of the present invention being worn by a person.

To use the knee strap of the present invention, one simply places the front side 18 of the main body portion 12 of the strap against the back of the knee. (See FIG. 1.) The top arm 22 of the first pair of arms, containing the rubber tubing, is brought across the top of the kneecap 34 and the top arm 26 of the second pair of arms is placed on top of the arm 22 so that the VELCRO strip 44 on the front side 46 of the arm 26 engages with the VELCRO strip 36 on the back side 38 of the arm 22. The bottom arm 24 of the first pair of arms, containing the rubber tubing, is then brought across the bottom of the kneecap 34 and the bottom arm 28 of the second pair of arms is placed on top of the arm 24 so that the VELCRO strip 48 on the front side 50 of the arm 28 engages with the VELCRO strip 40 on the back side 42 of the arm 24. The tubes 30 and 32 within the first pair of arms 22 and 24, respectively, are now positioned above and below the kneecap 34, respectively, so as to apply pressure to the tendons there located.

Once the top arms 22 and 26 and the bottom arms 24 and 28 are joined together, respectively, an opening 52 is formed. (See FIG. 3.) Opening 52 allows the kneecap 34 to be exposed, thereby allowing the knee to move. freely while the strap provides the necessary pressure to the patellar tendons. The arms fits non-restrictively so that the person using the strap can function through almost the full range of his or her natural ability. Also, the arms may be adjusted so that the position of the tubes may be varied as needed by the wearer.

The knee strap of the present invention is constructed primarily from a fabric-covered neoprene and the main body portion and attached arms are formed substantially from the same piece of neoprene. It should be understood, however, that other materials may be used. Also, the knee strap may differ in size, however, the arms should always be of sufficient length to be secured in the front of the leg for holding the knee strap upon the knee.

One of the benefits of the present invention is that the kneecap mechanism is strengthened by applying pressure on the tendon above the kneecap as well as below the kneecap. This tends to reduce the forces of the quadriceps on the patella tendon and erosion of the under surface of the kneecap due to a possible misalignment of the quadriceps. Another benefit of the present invention is that because of the nature of the material used, i.e., neoprene, the device applies constant dynamic forces to the surrounding areas of the knee joint, thus reducing the likelihood of Iliotibia Band and overuse syndromes prevalent in very active people.

The present invention may be embodied in other specific forms without departing from the spirit or essential attributes thereof and accordingly, reference should be made to the appended claims rather than to the foregoing specification as indicating the scope of the invention.

I claim:

1. A knee strap for supporting a knee and providing pressure to the patellar tendons above and below a person's kneecap comprising:

a main body portion having a first side and a second side;

a first pair of elongated arms extending from and attached to said first side of said main body portion;

a second pair of elongated arms extending from and attached to said second side of said main body portion;

means for securing said first pair of arms to said second pair of arms; and resilient compressible buttress means for applying pressure to the patellar tendons, said pressure applying means being located only within said first pair of arms and being adapted to lie only above and below the kneecap so that pressure is applied only above and below the kneecap during use.

2. The knee strap of claim 1 wherein said securing means includes hook and loop fasteners.

3. The knee strap of claim 1 wherein said pressure applying means includes a rubber tube within each of said first pair of arms.

4. The knee strap of claim 1 further including an opening for the kneecap.

5. The knee strap of claim 1 wherein said first pair of arms includes a top arm and a bottom arm and the second pair of arms includes a top arm and a bottom arm.

6. The knee strap of claim 5 wherein said securing means are attached to said top and bottom arms so that said top arms engage with each other and said bottom arms engage with each other.

* * * * *